United States Patent [19]

Franklin

[11] 4,094,020
[45] June 13, 1978

[54] URINE SPECIMEN COLLECTOR

[76] Inventor: Howard Franklin, 3365 Chisholm Tr., Boulder, Colo. 80302

[21] Appl. No.: 717,580

[22] Filed: Aug. 26, 1976

[51] Int. Cl.² .................. E03D 13/00; G01N 1/18; G01N 33/16

[52] U.S. Cl. .................. 128/294; 128/2 F; 128/295; 4/144.1; 4/144.3

[58] Field of Search .................. 4/110, 109; 128/295, 128/2 F; 215/6

[56] References Cited

U.S. PATENT DOCUMENTS

| | | | |
|---|---|---|---|
| 3,499,327 | 3/1970 | Lane | 4/110 X |
| 3,722,503 | 3/1973 | Hovick | 4/110 X |
| 3,830,107 | 8/1974 | Linzer | 128/2 F X |
| 3,831,453 | 8/1974 | McWhorter | 128/2 F X |
| 3,832,738 | 9/1974 | Kliemann | 4/110 |
| 3,929,412 | 12/1975 | Villari | 4/110 X |
| 4,026,433 | 5/1977 | Crippa | 4/110 X |

Primary Examiner—Richard E. Aegerter
Assistant Examiner—Stuart S. Levy
Attorney, Agent, or Firm—Hugh H. Drake

[57] ABSTRACT

A urine specimen collector includes first and second tubes disposed alongside one another. The first tube is closed at its lower end and has a mouth at its upper end engageable around the urethral orifice. The second tube is open at its lower end. A duct passes an overflow of urine from the first tube into the second tube. Disposed within the first tube is means that enables retention of a terminal portion of urine flow within that first tube.

17 Claims, 23 Drawing Figures

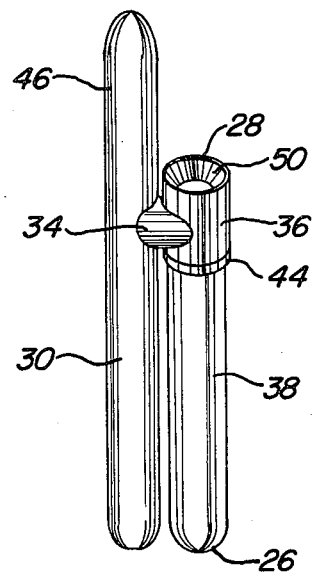
Fig_1
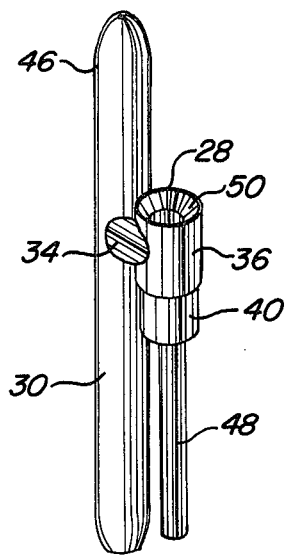
Fig_2
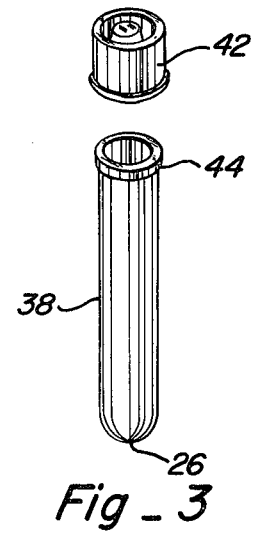
Fig_3
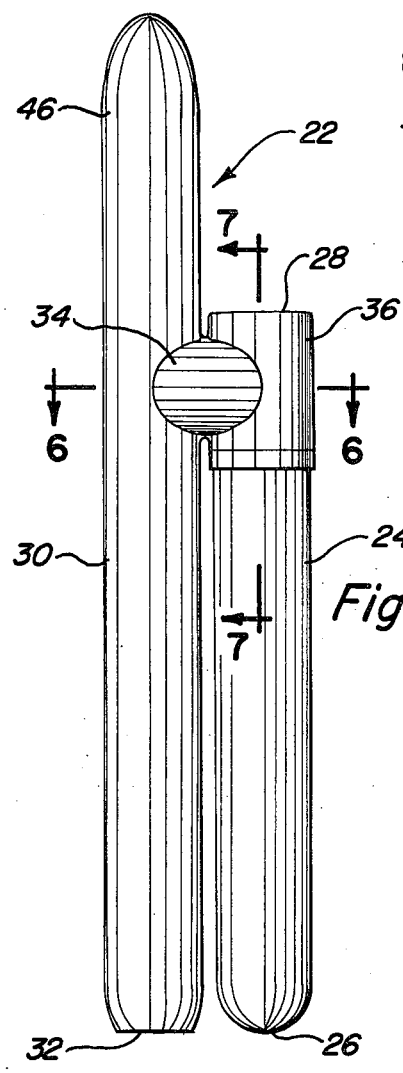
Fig_4
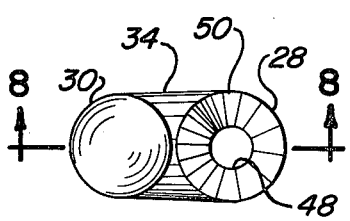
Fig_5
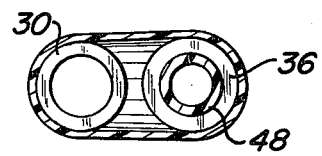
Fig_6
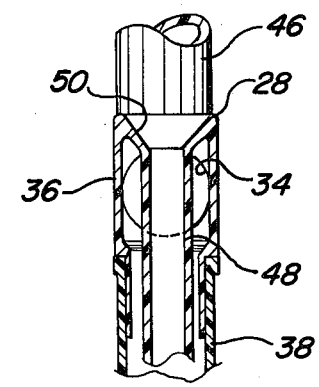
Fig_7
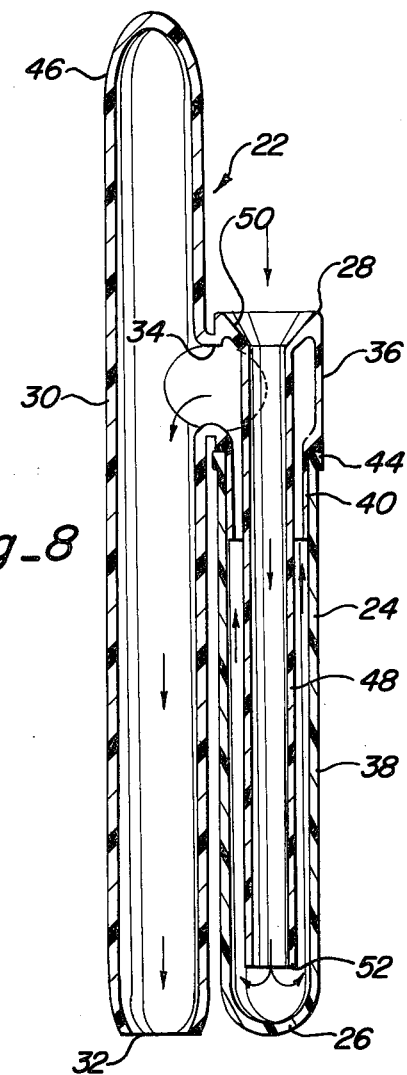
Fig_8

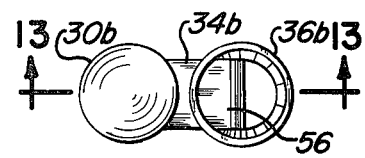
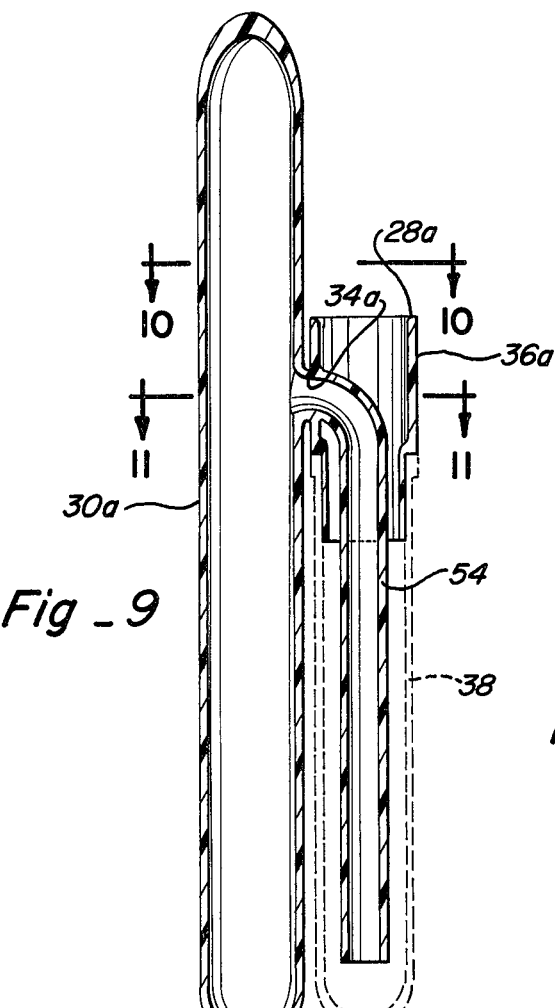
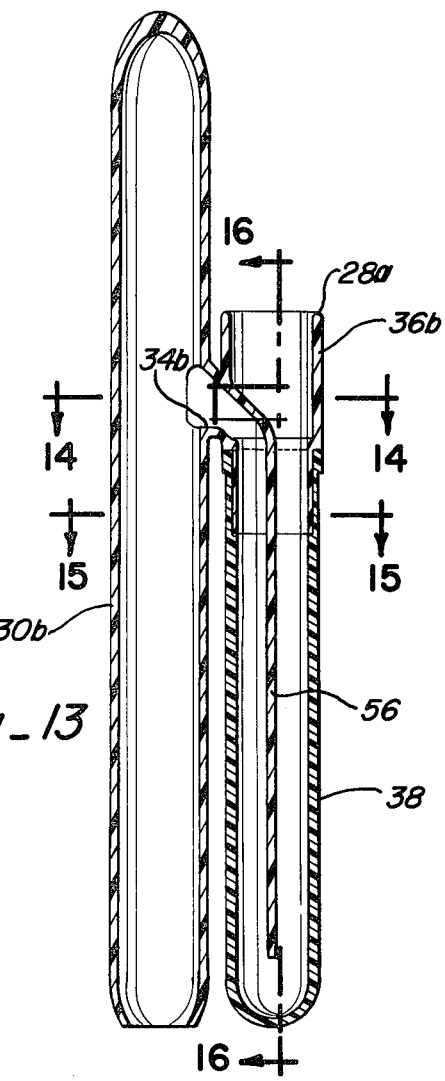
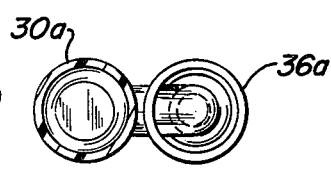
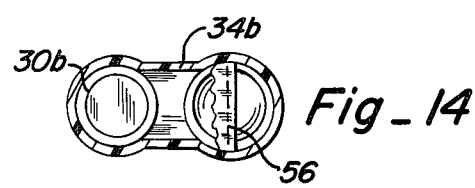
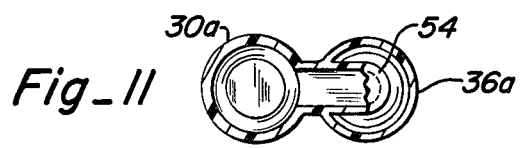
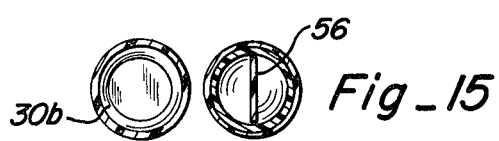

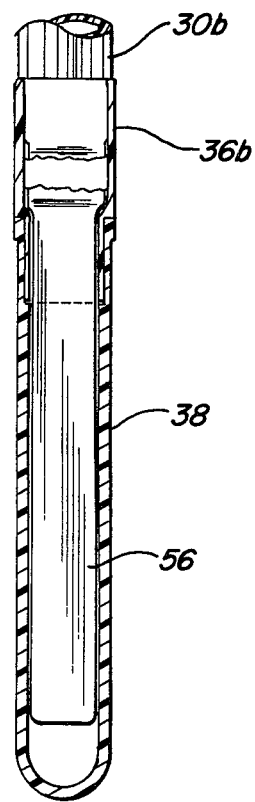
Fig_16
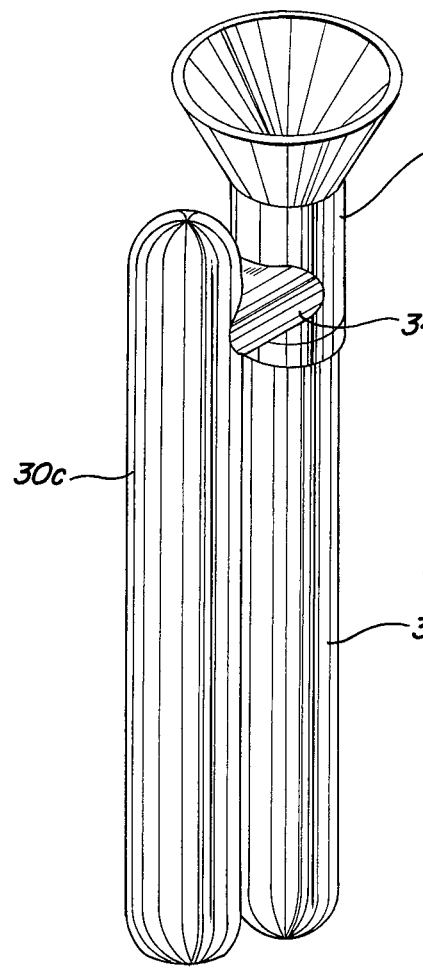
Fig_17
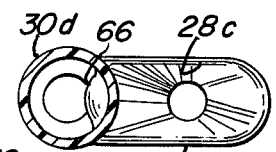
Fig_23
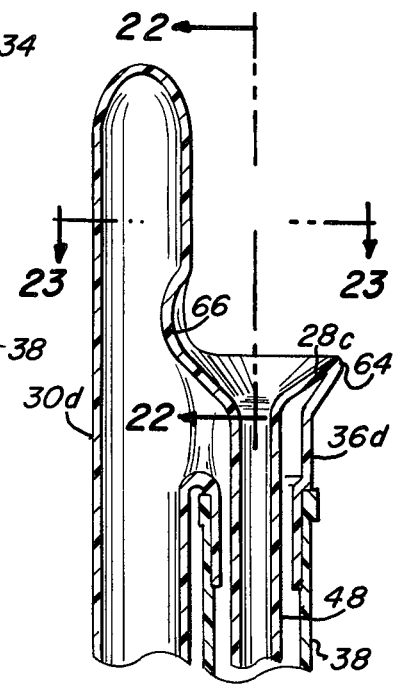
Fig_21
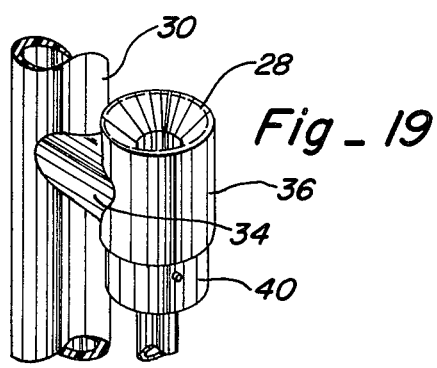
Fig_19
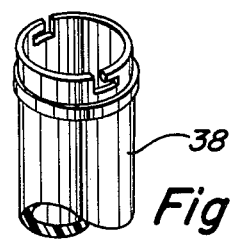
Fig_20
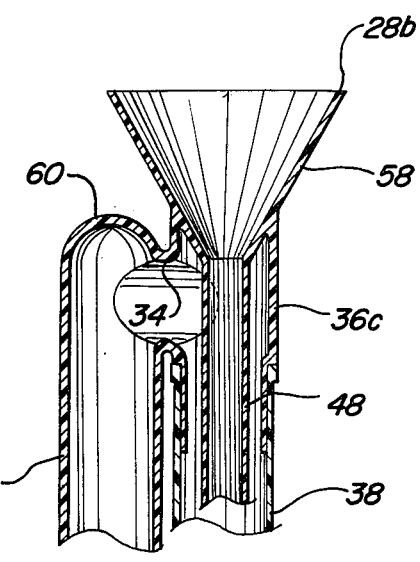
Fig_18
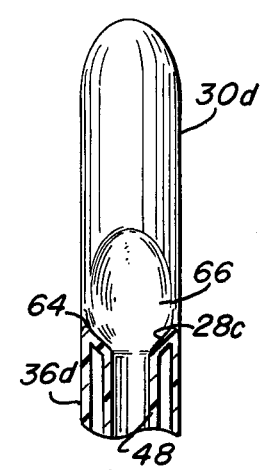
Fig_22

URINE SPECIMEN COLLECTOR

The present invention relates to a urine specimen collector. More particularly, it pertains to a collector that retains for examination only a later or terminal portion of the total urine flow.

In the human female, the urethral orifice is just superior to or above the vaginal opening. Most urine collection systems actually in use consist simply of a cylindrical container or collection cup. In order to obtain a urine specimen, the woman is requested to urinate into that cup. For securing as clean a urine specimen as possible, the woman usually is asked to first clean the vaginal area with some form of disposable sterile towel. This is for the purpose of removing secretions that otherwise might be washed into the collection cup along with the urinary stream. The woman is instructed for purposes of collection to separate the labia majora and labia minora with her fingers. The labia majora consists of longitudinal folds of skin and forms the outermost external portion of the female genital. The labia minora are two smaller folds between the labia majora. Both of those tissue structures surround the vaginal and the urethral orifices. If those structures are not manually separated, the urine may come in contact with them prior to reaching the collection cup and thereby become contaminated with bacteria, red and white blood cells or other debris. Of course, any such contamination might result in faulty analysis.

Moreover, the woman is instructed to urinate into the toilet before urinating into the collection cup. This is done in order hopefully to wash away the first portion of the urinary stream vaginal secretions, bacteria or other debris that still remain in and around the urethra. While still so urinating, the woman is yet further instructed to place the collection cup in front of the urine stream so as to collect the specimen for analysis which typically is of an amount of 12 cubic centimeters. Moreover, she also is instructed to remove the collection cup before completing urination and thereafter to finish such urination into the toilet upon which she is seated. This latter request is based upon the fact that the terminal portion of the urinary stream flow is not as strong as the midportion, as a result of which the stream tends to deviate in direction toward termination whereupon it may undesirably course over the labia minora and labia majora or other portions of the genital area not adequately washed with the initially discarded portion of the urinary stream.

All of these different steps in the collection process constitute an effort to avoid invalidating the analysis of the specimen. For example, externally derived contaminates might lead the diagnostician into falsely believing that the contaminates came from somewhere internally within the urinary tract system. If it were not known that such external contamination had occurred, unnecessary treatment or at least the inconvenience of repeated tests might result.

It has been recognized previously that urine specimens, especially those collected from females, are highly subject to such contamination unless done exactly in accordance with instructions. To that end, urethral catheterization is sometimes utilized. Of course, that involves patient discomfort and the possibility of at least trauma if not actual injury. In some cases, a female patient is placed into examining stirrups, the vaginal area is cleaned, the labia majora and minora are held apart, and the attendant thereafter attempts to manually catch a midstream collection sample literally in midair. Of course, that is at least both embarrassing and subject to undesired spillage. Still another way to obtain an uncontaminated urine specimen is to insert a needle through the skin and directly into the bladder, withdrawing the urine into a syringe. This method involves patient discomfort as well as injury.

Recognizing the foregoing and associated or related problems connected with obtaining a proper urine specimen, a variety of devices have heretofore been suggested. To avoid having to pass a specimen collector into and out of the flowing urine stream, it is known to attach an upwardly extending tubular portion to the specimen container and also to include an overflow drain. In one such approach, the upward extension is especially shaped so as to be engageable over the entire surface area surrounding the labia majora. Another prior approach employs a tube projecting upwardly from the specimen container with the upper end of that tube fitted with a resilient ring intended to be seated around the urethral orifice and also having a shoulder at one side that is utilized as a positioning aid by placing the shoulder against the distal end of the interior vaginal wall. Various other prior arrangements are known in which some kind of upwardly-extending protuberence is vaginally received so as to achieve alignment of the urethral orifice with an opening which leads to a container.

Included within the teachings of the prior art is express recognition of the aforenoted problems of increased likelihood of contamination of both the initial and terminal portions of the total urine flow. One earlier approach utilizes a combination of inner and outer bags or similar containers selectively connectable to an inlet and arranged so that only the mid-stream portion of the urine flow is trapped in one of the bags. Exemplary of this technique are U.S. Pat. Nos. 3,635,091 and 3,830,107. Still different mechanical approaches are described in U.S. Pat. No. 3,722,503. In one version of the latter, the initial portion of the urine stream is trapped in one cavity within the device while the later portion is allowed to overflow from a collecting tube into another cavity, the latter cavity also being fitted with an overflow exit. In a modified version, the urine is initially collected in a main cavity and only after the level within that cavity reaches a certain height is the urine permitted to overflow into a second collection cavity which later may be sealed off before the entire device is transported to the laboratory for analysis. While apparatus of this sort is certainly meritorious in terms of the principles sought to be implemented, it at the same time poses complexity, and related undue expense of construction and assembly while also being cumbersome and awkward to use.

It is, accordingly, a general object of the present invention to provide a new and improved urine specimen collector that achieves the benefits of the aforenoted prior approaches while yet avoiding their disadvantages.

A specific object of the present invention is to provide a new and improved urine specimen collector that is exceedingly compact, inexpensive and easy to use.

A related object of the present invention is to provide such a urine specimen collector that enables the user readily to obtain an uncontaminated specimen easily and without any requirement of extensive instruction or assistance.

Another object of the present invention is to provide a new and improved urine specimen collector having many of the foregoing advantages and which also is particularly modified so as to be more readily utilized in collecting the specimen from the male.

A urine specimen collector constructed in accordance with the present invention includes a first tube closed at its lower end and having a mouth at its upper end engageable around the urethral orifice; a second tube is disposed alongside the first tube and is open at its lower end. A duct passes an overflow of urine from the first tube into the second tube. Disposed within the first tube is means for enabling retention of a terminal portion of urine flow within that first tube.

The features of the present invention which are believed to be novel are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 1 is a perspective view of one embodiment of a urine specimen collector;

FIG. 2 is a perspective view of one portion of the assembly shown in FIG. 1;

FIG. 3 is a perspective view of another portion of the assembly shown in FIG. 1, together with an added closure member for that portion;

FIG. 4 is a side-elevational view of the embodiment shown in FIG. 1 and as assembled for use;

FIG. 5 is a top plan view of the embodiment of FIG. 4;

FIG. 6 is a cross-sectional view taken along the line 6—6 in FIG. 4;

FIG. 7 is a fragmentary cross-sectional view taken along the line 7—7 in FIG. 4;

FIG. 8 is a cross-sectional view taken along the line 8—8 in FIG. 5;

FIG. 9 is a view taken the same as FIG. 8 but of a modified version of the collector;

FIG. 10 is a cross-sectional view taken along the line 10—10 in FIG. 9;

FIG. 11 is a cross-sectional view taken along the line 11—11 in FIG. 9;

FIG. 12 is a top plan view taken the same as FIG. 5 but of still another modified version of the collector;

FIG. 13 is a cross-sectional view taken like the views of FIGS. 8 and 9 but of the further modified version of FIG. 12;

FIG. 14 is a cross-section view taken along the line 14—14 in FIG. 13;

FIG. 15 is a cross-sectional view taken along the line 15—15 in FIG. 13;

FIG. 16 is a fragmentary cross-section view taken along the line 16—16 in FIG. 13;

FIG. 17 is a perspective view of a still different embodiment of a urine specimen collector;

FIG. 18 is a fragmentary cross-section view taken longitudinally through the embodiment of FIG. 17;

FIG. 19 is an enlarged fragmentary perspective view of a portion of the collector as shown in FIG. 2;

FIG. 20 is an enlarged fragmentary perspective view of a portion of one of the components shown in FIG. 3;

FIG. 21 is a fragmentary perspective view of a collector generally like that of FIGS. 1-7, but having one of its components in modified form;

FIG. 22 is a fragmentary cross-sectional view taken along the line 22—22 in FIG. 21; and FIG. 23 is a cross-sectional view taken along the line 23—23 in FIG. 21.

With reference to a first embodiment as shown in assembled form in FIG. 4, a urine specimen collector 22 includes a first tube 24 closed at its lower end 26 and having a mouth 28 at its upper end engageable around the urethral orifice. A second tube 30 is disposed alongside tube 24 and is open at its lower end 32. Preferably, the upper end of tube 30 tapers smoothly to a rounded closure.

A duct 34 extends from an upper portion of the lateral wall of the tube 24 through an upper portion of the lateral wall of tube 30 and specifically into an intermediate portion of the latter. The connecting structure of duct 34 serves as the sole mechanical connection between tubes 24 and 30.

Tube 24 includes an upper segment 36 physically secured by duct 34 to tube 30 and a lower segment 38 removably attached to upper segment 36 and serving as the ultimate specimen container. To that end, the lower portion of segment 36 is necked down as at 40 so as to be received within the upper end portion of segment 38. To the end of removable attachment, tolerances may be arranged so that segment 38 is simply slipped over portion 40 and frictionally retained in place. In the alternative, a different mode of fastening may be employed such as screw threads or the bayonet-type coupling specifically illustrated in FIGS. 19 and 20.

Separate from the assembly itself as assembled in the illustration of FIG. 4 is a cap 42 as shown in FIG. 3. Cap 42 in this case is frictionally engageable with a slightly enlarged upper rim 44 on the upper end of segment 38. Accordingly, segment 38 may be removed from the remainder of the assembly, capped and sent solely by itself to a laboratory for analysis. If desired, the wall of segment 38 may be provided with a series of longitudinally spaced marks so as to indicate the different volume levels in segment 38 serving as the container.

Tube 30 includes an upper end portion 46 that projects above mouth 28 at the upper end of tue 24. Duct 34 spaces tubes 24 and 30 laterally apart by a distance such that insertion of upper end portion 46 into the vagina of the female serves to align mouth 28 with the urethral orifice.

Still another tube 48 is joined at its upper end by an outwardly flaring region 50 to mouth 28 at the upper rim of segment 36. Tube 48 projects downwardly and is spaced within the wall of tube 24. At its lower open end 52, tube 48 is spaced above lower end 26 of segment 38 of tube 24. Tube 48 serves to enable the retention of a subsequent or later portion of urine flow within segment 38 of tube 24. In use, urine flow directed into mouth 28 courses downwardly through tube 48, then upwardly within tube 24 and exterior of tube 48 to a point of overflow through duct 34 and finally down and out the bottom of tube 30 for discharge of the overflow into a toilet or other receptacle upon which the user is situated.

The embodiment of FIGS. 9-11 is quite similar in external appearance and arrangement. As before, a third tube 54 projects downwardly toward the bottom of segment 38 of the first tube and has its lower open end spaced above the lower end of segment 38. In this case, however, tube 54 is joined at its upper end to duct 34a and becomes the inlet of that duct that leads to tube 30a. Thus, urine entering through mouth 28a of upper segment 36a flows downwardly within segment 38 and around the exterior of tube 54 and then rises upwardly within the interior of tube 54 and through duct 34a in its passage into the tube 30a so as to drain out of the open bottom end of the latter. Mouth 28a is in this case shaped simply like the upper rim of a cup instead of having the internal flare 50 of the first-described version. In this connection, it is to be noted that the advantage of vaginal orientation of the unit and parallel-tube orientation arranged for flushing and overflow may be had with other conformation of the mouth of the urine receiving tube. For example, and not as effective in avoiding contamination, the mouth may be formed into a much larger funnel.

In the still different version illustrated in FIGS. 12-16, a vane 56 projects downwardly from a duct 34b toward the bottom of segment 38. Vane 56 serves to enforce urine flow from mouth 28a around the lower end of the vane and then upwardly so as to overflow through duct 34b. To insure a complete flushing action of the initial urine flow, it is contemplated that vane 56 may be twisted, have its surface rippled or be otherwise formed or associated with additional structure for disrupting the flow path.

Because of the alignment function provided by the existence of the upwardly extending portion 46 of tube 30 (including 30a or 30b), the versions so far described are particularly designed to accommodate usage by the female. Nevertheless, they may also be used by the male. The male patient would simply place the end of his penis into mouth 28 or 28a so that his urethral orifice was properly aligned as he held the collector so as to permit overflow drainage into the toilet or the like. In that case, however, upwardly extending portion 46 of tube 30 becomes at least superfluous and may even prove to be inconvenient. Accordingly, the version of FIGS. 17 and 18 is particularly adapted for male use. Although any of the preceding internal arrangements of structure may be employed in this embodiment, that illustrated has the internal arrangement of tube 48 as already described with respect to FIGS. 1-8 and the cooperation of duct 34 that leads to a tube 30c. In this case, however, the upper end portion of segment 36c is flared outwardly to form a funnel 58 so as to better accommodate the end of the penis. In addition, the closed upper end 60 of tube 30c is disposed below mouth 28b at the upper end of segment 36c.

In usage of the female versions, the patient will first cleanse the vaginal area with some form of disposable sterile towel. She next positions hereself standing with her back to the toilet. She grasps the collector in either hand in a manner so that the shorter tube 24 is in front and the unit is held in an upright orientation. Upward extension 46 is then inserted into the vagina; if desired, a suitable lubricant may first be applied to extension 46. That operation necessitates the parting of her labia majora and minora. Portion 46 is inserted until the mouth of the shorter tube is firmly pressed against her tissue. As a result of the close anatomical approximation of the vagina and urethral orifice, the open mouth is cupped around the urethral orifice. She next sits on the toilet and the open bottom end of the longer tube 30 is placed within the toilet opening; urination then is begun. With the assembly correctly positioned, there is no problem in urination, and urination is continued fully until completed as normal. After urination, the entire collector may be placed back into a suitable container so as to be retained in an upright position in order to prevent spillage. Desirably, suitable instruction to that effect is printed on the exterior surface of the container or other package. Thereafter, the assembly is given to the attendant personnel who need only detach segment 38, affix cap 42, perhaps apply a label with the patient'name, time and date and forward only segment 38 with its cap to the laboratory.

The urine collection systems herein described have numerous advantages. When used, the urethral orifice is cupped so as to eliminate the risk of contamination as the urine flows by the labia majora and minora as well as other genital structure. Normally, it is somewhat difficult for a woman to locate her urethral orifice. However, the relationship between the two different primary tubes of the described collectors enables the female patient without difficulty to place the receiving mouth in the proper position around the urethral orifice. This also avoids difficulty in urinating into a comparatively small-diameter opening such as mouth 28.

The collection systems described necessitate that the patient inherently must spearate the labia majora and minora in order to collect the specimen. This keeps those structures separated thereby avoiding contact with the urinary stream through completion of the urination and thus insures against contamination thereform. Furthermore, any improper use of the collection system should normally become quite evident to the user. For example, if upwardly extending portion 46 is not inserted into the vaginal opening, or if the open mouth of the other tube is not positioned to the front, it is most likely that any specimen will be obtained at all. Even when insertion and orientation are generally correct, but the mouth is not closed around the urethral orifice, there will probably be significant leakage of urine around the sides of the collector and this should alert the properly instructed patient of improper collection. All in all, leeway for patient error in use of the system is minimized and, if immproperly used, the diagnostician would be alerted.

In use, contaminates from the initial flow of the urine are flushed entirely through the unit and discarded. Moreover, the terminal portion of the urinary stream, that which ends up remaining in segment 38, is prevented from being contaminated. This eliminates the need to attempt to collect a midstream portion.

In general, the approach as described permits the collection of the desired urine sample without any mess whatsoever. This is because all of the urine flow is conducted directly through the system and there is no need for attempting to aim or time the "catch" of only a portion of the total flow.

Also, a sample will be obtained even if the patient is able only to provide a small amount of total flow. Still further, the approach presently described eliminates any need to a make a subsequent transfer of the collected sample to a separate test tube or other container. Segment 38 serves entirely as such a test tube and may be put directly into a centrifuge or other analysis apparatus. Just this function may largely offset the cost of the collection system.

Moreover, any of the versions described above may conveniently be formed of a plastic or the like in such a way that, after amortization of modest and initial tooling costs, they can be made available at very reasonable expense. With sufficient volume, such costs may be sufficiently low as to permit discarding of all parts after onetime use. On the other hand, the different components are such as to permit ready sterilization should reuse be desirable.

While a significant portion of the description has been directed to utility with respect to usage by the female patient, it is at the same time quite apparent that many of the aforenoted advantages are present in connection with usage by the male patient. As indicated, the approach of FIGS. 17 and 18 is preferred for the male patient, although the other versions also may serve that purpose.

Finally, it was noted above that other conformations of the mouth of the urine receiving tube may be employed. FIGS. 21-23 depict what may prove to be a preferred form. In this case, mouth 28c has an upper margin 64 which is generally of oval shape. This increases the catch area for a given size of upper tube segment 36d. As illustrated, it also conveniently enables formation of the components so that one side of margin 64 is indented into the wall of tube 30d as indicated at 66. Alternatively, indentation 66 may be omitted and a portion of margin 64 modified adjacent to tube 30d (or 30, 30a or 30b) so as to be in the shape of a segment of a circle size to fit snugly against the tube wall. In either case, the arrangement includes means defining a snug interfitting between a portion of the mouth and the wall of the tube. The latter is helpful in the situation in which the urethral orifice is located extremely close to the wall of the vaginal opening. As illustrated in FIG. 21, oval-shaped mouth 28c is incorporated into a collector which otherwise is like the version shown in FIG. 1-7. Of course, any of the other versions similarly may utilize an oval mouth or cup.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A urine specimen collector comprising:
   a first tube closed at its lower end and having a mouth at its upper end engageable around the urethral orifice;
   a second tube disposed alongside said first tube and open at its lower end;
   a duct positioned for passing an overflow of urine from said first tube into said second tube;
   and means projecting downwardly within said first tube and having a lower end spaced above the the lower end of said first tube and below said duct for enabling retention of only a subsequent portion of urine flow within said first tube.

2. A collector as defined in claim 1 in which said duct extends from an upper portion of a lateral wall of said first tube into said second tube.

3. A collector as defined in claim 2 in which said duct extends through an upper portion of a lateral wall of said second tube.

4. A collector as defined in claim 2 in which said duct extends through an intermediate portion of a lateral wall of said second tube.

5. A collector as defined in claim 1 in which said duct serves as the sole mechanical connection between said first and second tubes.

6. A collector as defined in claim 1 in which said first tube includes an upper segment secured to said second tube and a lower segment removably attached to said upper segment and serving as a specimen container.

7. A collector as defined in claim 1 in which the upper end portion of said second tube projects above the upper end of said first tube and in which said tubes are laterally spaced so that insertion of said upper end portion of said second tube in the vagina serves to align said mouth with said orifice.

8. A collector as defined in claim 1 in which the upper end portion of said first tube is funnel shaped to accommodate receipt of the head of the penis.

9. A collector as defined in claim 1 in which the upper end of said second tube is below the upper end of said first tube.

10. A collector as defined in claim 1 in which said retention means includes a third tube joined at its upper end to said mouth, and spaced within the wall of said first tube.

11. A collector as defined in claim 1 in which said retention means includes a third tube joined at its upper end to said duct that leads to said second tube, said third tube and spaced within the wall of said first tube.

12. A collector as defined in claim 1 in which said retention means includes a vane projecting from said duct toward the bottom of said first tube and directing urine flow from said mouth around the lower end of said vane and then upwardly into said duct.

13. A collector as defined in claim 1 in which the lower end portion of said first tube is removable to serve as a specimen collector, and which further includes a cap sealingly attachable to close said lower end portion.

14. A collector as defined in claim 1 in which said mouth is of generally oval shape.

15. A collector as defined in claim 14 which further includes means defining a snug interfitting between a portion of said mouth and the wall of said second tube.

16. A collector as defined in claim 15 in which said defining means includes an indentation in said wall into which is received said portion of said mouth.

17. A collector as defined in claim 1 which further includes means defining a snug interfitting between a portion of said mouth and the wall of said second tube.

* * * * *